(12) United States Patent
Liao et al.

(10) Patent No.: US 8,722,921 B2
(45) Date of Patent: May 13, 2014

(54) PROCESS FOR REDUCTION OF ALPHA-ACYLOXY SULFIDE DERIVATIVES

(75) Inventors: JyhHsiung Liao, Hsinchu (TW); LungHuang Kuo, Tainan (TW)

(73) Assignee: ScinoPharm Singapore PTE, Ltd., Singapore (SG)

( * ) Notice: Subject to any disclaimer, the term of this patent is extended or adjusted under 35 U.S.C. 154(b) by 0 days.

(21) Appl. No.: 13/405,130

(22) Filed: Feb. 24, 2012

(65) Prior Publication Data

US 2012/0220784 A1    Aug. 30, 2012

Related U.S. Application Data

(60) Provisional application No. 61/447,391, filed on Feb. 28, 2011.

(51) Int. Cl.
    *C07C 229/22*      (2006.01)

(52) U.S. Cl.
    CPC .................................. *C07C 229/22* (2013.01)
    USPC .......................................................... 560/37

(58) Field of Classification Search
    CPC .................................................... C07C 229/22
    USPC ............................................................ 560/37
    See application file for complete search history.

(56) References Cited

U.S. PATENT DOCUMENTS

| | | | |
|---|---|---|---|
| 5,705,671 A | 1/1998 | Suzuki et al. | |
| 5,883,284 A * | 3/1999 | Suzuki et al. | 560/16 |
| 6,239,308 B1 | 5/2001 | Suzuki et al. | |
| 6,278,002 B1 * | 8/2001 | Okuro et al. | 549/520 |
| 6,683,214 B2 | 1/2004 | Onishi et al. | |
| 2001/0018532 A1 | 8/2001 | Okuro et al. | |
| 2003/0087831 A1 | 5/2003 | Ohmoto et al. | |

FOREIGN PATENT DOCUMENTS

EP    1 050 532 A2    11/2000

OTHER PUBLICATIONS

Suzuki et al. (J. Org. Chem., 2005, 70, 7317-7323).*
Tai et al. (Org. Lett., 6 (2004), p. 2905-2908).*
March's Advanced Organic Chemistry, 5th ed., (2001), Chapters 10 and 16, p. 1566 provided.*
Ho et al., Bioorg. Med. Chem. Lett., 1995, vol. 5, pp. 2959-2962.
Badorrey, Tetrahedron Asym., 2009, vol. 20, pp. 2226-2229.
Izawa et al., "Industrial syntheses of the central core molecules of HIV protease inhibitors," Chem. Rev. 2006, vol. 106, pp. 2811-2827.
Suzuki "An efficient synthesis of N-protected threo (2R,3S)-3-amino-1,2-epoxy phenylbutane," Tetrahedron Letters, 2005, vol. 46, pp. 5811-5814.
PCT application No. PCT/SG2012/000055, International Search Report and Written Opinion, mailed Aug. 3, 2012 , 6 pages.

* cited by examiner

*Primary Examiner* — Robert Havlin
(74) *Attorney, Agent, or Firm* — Kilpatrick Townsend & Stockton LLP

(57) ABSTRACT

The present invention provides an efficient and scalable process to prepare the compound of formula 4 by reduction of the corresponding α-acyloxy sulfides.

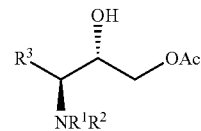

9 Claims, 2 Drawing Sheets 1a ($R^1$ = H, $R^2$ = Boc, $R^3$ = Bn, $R^4$ = CH$_3$)
1b ($R^1$ = H, $R^2$ = Cbz, $R^3$ = Bn, $R^4$ = CH$_3$)
1c ($R^1$ = $R^2$ = $R^3$ = $R^4$ = Bn)
1d ($R^1$ = H, $R^2$ = Boc, $R^3$ = CH$_3$, $R^4$ = CH$_3$)
1e ($R^1$ = H, $R^2$ = Boc, $R^3$ = CH(CH$_3$)$_2$, $R^4$ = CH$_3$)
1f ($R^1$ = H, $R^2$ = Boc, $R^3$ = CH$_2$CH(CH$_3$)$_2$, $R^4$ = CH$_3$)
1g (-$R^1R^3$- = -(CH$_2$)$_3$-, $R^2$ = Boc, $R^4$ = CH$_3$)

PROCESS FOR REDUCTION OF ALPHA-ACYLOXY SULFIDE DERIVATIVES

CROSS-REFERENCES TO RELATED APPLICATIONS

This application claims priority from U.S. Provisional Patent Application Ser. No. 61/447,391, which was filed on Feb. 28, 2011. The entire content of U.S. Provisional Patent Application Ser. No. 61/447,391 is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Conventional methods for synthesizing chiral aminoepoxides (e.g. the compounds of formulae 6 or 8, shown in FIGS. 2 and 3), using chiral amino acids and their derivatives as starting materials, are well known (*Chem. Rev.* 2006, 106, 2811-2827). Several general synthetic strategies for preparing α-amino epoxides are reported, including erythro selective chloromethylation of phenylalaninal derivatives; erythro selective reduction of halomethyl ketones (see U.S. Pat. No. 6,683,214 and EP 1 050 532); direct reduction of α-amino aldehydes by sulfonium ylides; epoxidation of allylamines; and reductive amination of keto epoxides. Nonetheless, in most of these cases, only one of the diastereomers (erythro or threo) is available.

Thus, there exists an unmet need for methods providing key precursors that can be easily converted to both erythro and threo chiral aminoepoxides from easily available starting materials. The present invention addresses this and other needs.

BRIEF SUMMARY OF THE INVENTION

In one aspect, the present invention provides a process for preparing a compound of formula 4:

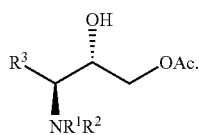

The process includes contacting a compound of formula 3:

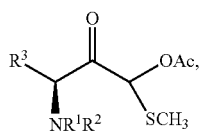

with a reducing agent to produce said compound of formula 4, wherein
R$^1$ is selected from the group consisting of hydrogen, branched or unbranched C$_1$-C$_6$ alkyl and C$_7$-C$_{18}$ aralkyl;
R$^2$ is an amine protecting group; and
R$^3$ is selected from the group consisting of branched or unbranched C$_1$-C$_6$ alkyl and C$_7$-C$_{18}$ aralkyl, or
R$^3$ and R$^1$ together form a 4- to 7-membered cyclic group having from 3 to 6 carbon atoms.

In a second aspect, the present invention provides novel compounds that are intermediates or products of the inventive process.

BRIEF DESCRIPTION OF THE DRAWINGS

FIG. 2 shows the scheme for the synthesis of epoxide 6 from (3S)-3-([(1,1-dimethylethyl)oxy]carbonylamino)-2-hydroxy-4-phenylbutyl ethanoate 4a.

FIG. 3 shows the scheme for the synthesis of epoxide 8 from (3S)-3-([(1,1-dimethylethyl)oxy]carbonylamino)-2-hydroxy-4-phenylbutyl ethanoate 4a.

DETAILED DESCRIPTION OF THE INVENTION

I. General

The present invention provides a process for the preparation of (2S,3S)-1-O-acyl-3-aminoalkane-1,2-diols of formula 4:

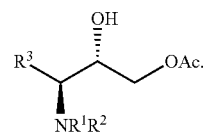

Figure 1:
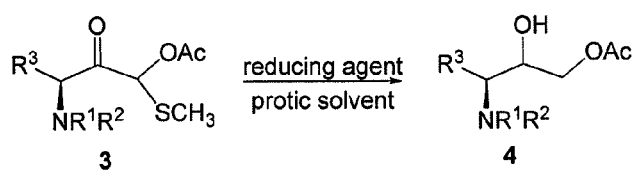
FIG. 1 shows the key reduction step for the synthesis of (2S,3S)-1-O-acyl-3-aminoalkane-1,2-diols from the corresponding α-acyloxy sulfides.

Such compounds are valuable building blocks for the synthesis of various biologically active molecules including protease inhibitors, glycosphingolipids, and polyhydroxylated nitrogen heterocycles. The (2S,3S)-1-O-acyl-3-aminoalkane-1,2-diols 4 are accessed from convenient starting materials via an efficient, scalable process based on the reduction of the corresponding α-acyloxy sulfides 3 (FIG. 1).

II. Definitions

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "reducing agent" refers to an agent capable of reducing another compound. The reducing agent can be a metal, an organic compound, or a complex of a metal and an organic compound. Examples of reducing agents include, but are not limited to, alkali metals, metal hydrides, thiol- and phosphine-based reducing agents, ascorbic acid, and the like.

The term "alkyl," by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the terms "aryl" and "aromatic ring," by themselves or as part of another substituent, refer to a poly-unsaturated, hydrocarbon group which can be a single ring or multiple rings (up to three rings) which are fused together or linked covalently. Non-limiting examples of aryl groups include phenyl, naphthyl and biphenyl.

The terms "arylalkyl" and "aralkyl" are used interchangeably to refer to a radical having an alkyl component and an aryl component, where the alkyl component links the aryl component to a molecule. The alkyl component is as defined above, except that the alkyl component is at least divalent in order to link to the aryl component to the remainder of the molecule. The aryl component is as defined above. Examples of arylalkyl groups include, but are not limited to, benzyl and phenylethyl.

As used herein, the term "protecting group" refers to a moiety that renders a functional group unreactive, but is also removable so as to restore the functional group to its original state. A protecting group can be an "amine protecting group" wherein the protected functional group is an amine. Examples of amine protecting groups include, but are not limited to, 9-fluorenylmethyl carbamoyl, t-butyl carbamoyl, benzyl carbamoyl, acetyl, phthalimido, benzyl, triphenylmethyl, and p-toluenesulfonyl. Various protecting groups, including amine protecting groups, are well known to one of ordinary skill in the art and include compounds that are disclosed in *Protective Groups in Organic Synthesis*, 4th edition, T. W. Greene and P. G. M. Wuts, John Wiley & Sons, New York, 2006, which is incorporated herein by reference in its entirety.

III. Embodiments of the Invention

The present invention discloses an efficient and scalable process for synthesizing (2S,3S)-1-O-acyl-3-aminoalkane-1, 2-diols 4 by reduction of the corresponding α-acyloxy sulfides 3, which are easily prepared via known methods (see, for example: *Tetrahedron Letters*, 2005, 46, 5811-5814; U.S. Pat. No. 5,705,671).

Accordingly, the present invention provides a process for the preparation of a compound of formula 4:

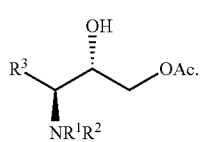

The process includes:
contacting a compound of formula 3:

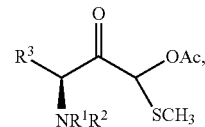

with a reducing agent under conditions sufficient to form the compound of formula 4, wherein in each of compounds 3 and 4, $R^1$ is selected from the group consisting of hydrogen, branched or unbranched $C_1$-$C_6$ alkyl, and $C_7$-$C_{18}$ aralkyl;

$R^2$ is an amine protecting group; and $R^3$ is selected from the group consisting of branched or unbranched $C_1$-$C_6$ alkyl and $C_7$-$C_{18}$ aralkyl; or $R^3$ and $R^1$ together form a 4- to 7-membered cyclic group having from 3 to 6 carbon atoms.

In some embodiments, $R^2$ is selected from the group consisting of t-butoxycarbonyl (Boc), benzyloxycarbonyl (Cbz), methoxycarbonyl (Moc), and benzyl (Bn).

The reaction described above can be carried out in the presence of a protic solvent such as an alcohol (MeOH, EtOH, iPrOH, etc.), water, or aqueous THF, as well as combinations of those solvents. In some embodiments, the reaction is carried out in the presence of ethanol and water.

Preferably, the reducing agent is lithium aluminum hydride (LAH) or sodium borohydride ($NaBH_4$). In some embodiments, the reducing agent used in the present invention is sodium borohydride.

The present invention is easy and safe to handle when using reducing agents and aqueous protic solvents as provided herein. The process is conducted at anywhere from about −40° C. to around room temperature, conditions which are easily and efficiently maintained on the laboratory scale as well as the industrial scale. Advantageously, the compounds of formula 4 can be economically purified by the simple means of crystallization, in contrast to previously disclosed methods that rely on expensive chromatographic steps (*Tetrahedron Letters*, 2005, 46, 5811-5814).

Figure 2:
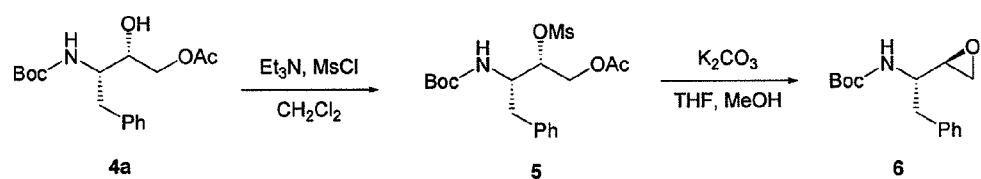
Figure 3:
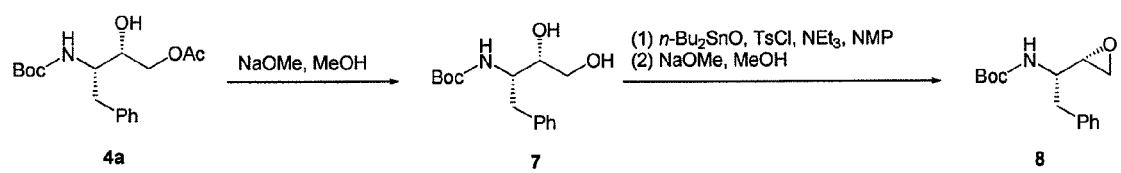

The inventive methods are particularly useful because compounds of formula 4 can be easily converted into both erythro and threo epoxides, which in turn can provide access to various biologically active molecules and building blocks for pharmaceuticals. In some embodiments, for example, the compound of formula 4a is a precursor of both chiral aminoepoxides 6 and 8 (FIG. 2 and FIG. 3, respectively). Another characteristic of the present invention is the protection of the 1-hydroxyl group prior to reduction, which reduces the overall number of steps required to produce chiral aminoepoxides, as compared with the method provided in *Tetrahedron Letters*, 2005, 46, 5811-5814.

The conversion of compound 4a to the compounds 6 and 8 can be conducted by known methods (see U.S. Pat. No. 6,278, 002; *Bioorg. Med. Chem. Lett.* 1995, 5, 2959-2962; *Tetrahedron Asym*, 2009, 20, 2006-2229).

Figure 4:
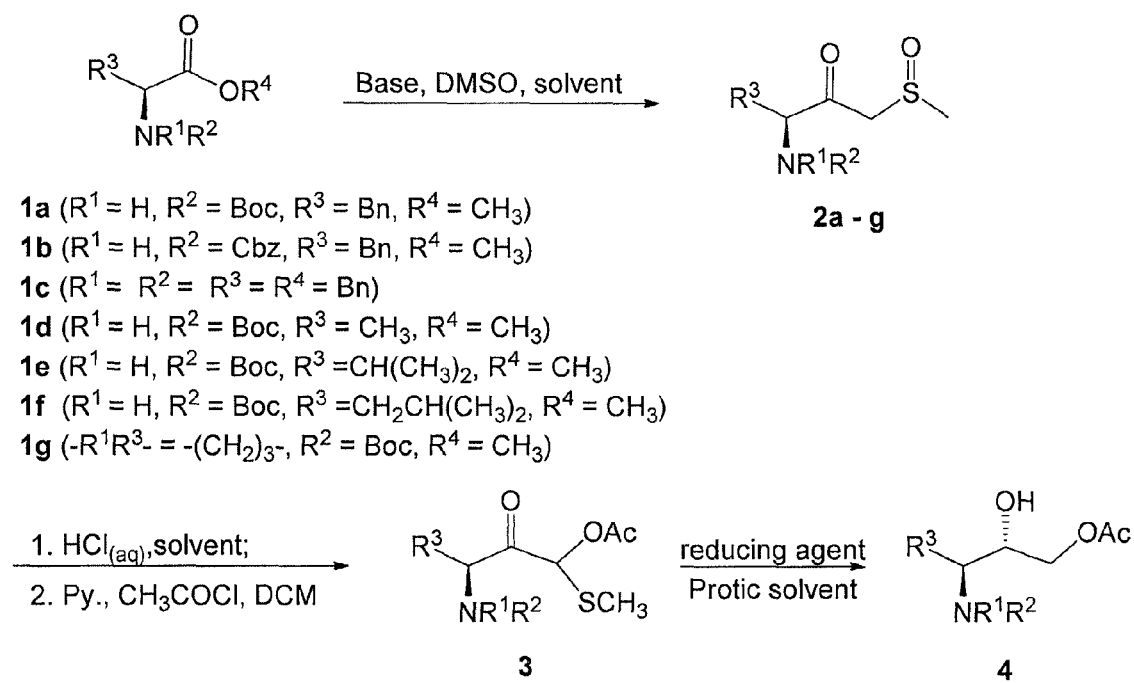
FIG. 4 shows the scheme for the synthesis of various (2S, 3S)-1-O-acyl-3-aminoalkane-1,2-diols from convenient starting materials.

FIG. 4 shows the synthetic process from the starting materials to the target (2S,3S)-1-O-acyl-3-aminoalkane-1,2-diols 4. Accordingly, the present invention also provides one or more of the following compounds:

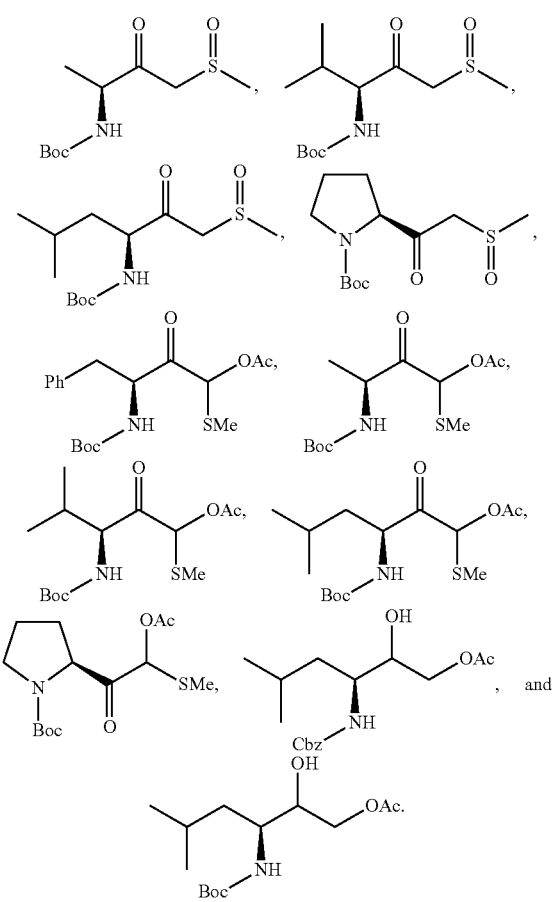

IV. Examples

The following examples are provided for the purpose of further illustration only and are not intended to be limitations on the disclosed invention.

Examples 1-7 illustrate the preparation of compounds 2a through 2g as shown in FIG. 4.

Example 1

Preparation of 1,1-dimethylethyl N-[(1S)-3-(methylsulfinyl)-2-oxo-1-(phenylmethyl)propyl]carbamate 2a To a suitable reactor was added THF (7.8 L) and NaNH$_2$ (0.77 kg, 4.0 equiv) at 20-30° C. under N$_2$. The white slurry was heated to 60-70° C. DMSO (5.8 L, 17.7 equiv) in THF (7.8 L) solution was added at 60-70° C., and the mixture was stirred at this temperature for 2 hr. The mixture was cooled to −5-5° C. Ester 1a (1.00 kg, 1.00 equiv) in toluene solution was added at −5-5° C., and the mixture was stirred at this temperature for 1 hr. The reaction was deemed completed as determined by HPLC. 10% citric acid aqueous solution (15.6 L) was added at 20-30° C., and the mixture was stirred at this temperature for 30 min. The separated organic layer was washed with 20% NaCl aqueous solution (13 L). The separated organic portion was concentrated at 35-45° C. under reduced pressure until the volume reached about 6 L. n-Heptane (12 L) was added at 20-30° C. over 1 hr, and the mixture was stirred at this temperature for 3 hr. The mixture was filtered, and the filtered cake was washed with n-heptane (5 L). After being dried at 40-50° C. under reduced pressure, a diastereomeric mixture of 2a (1.2 kg, 80% yield) with purity greater than 98% was obtained.

$^1$H NMR (400 MHz, CDCl$_3$) δ 7.23-7.11 (m, 5H), [5.90 (broad, minor isomer), 5.72 (m, major isomer), totaling 1H], 4.34-4.31 (m, 1H), 3.94 (d, J=15 Hz, 1H), 3.73 (d, J=15 Hz, 1H), 3.11-3.04 (m, 1H), 2.87-2.81 (m, 1H), [2.57 (s, major isomer), 2.55 (s, minor isomer), totaling 3H], 1.32 (s, 9H)

Example 2

Preparation of phenylmethyl N-[(1S)-3-(methylsulfinyl)-2-oxo-1-(phenylmethyl)propyl]carbamate 2b To a suitable reactor was added THF (52 mL) and NaH (60%, 7.66 g, 3.0 equiv) at 20-30° C. under N$_2$. The white slurry was heated to 60-70° C. DMSO (52 mL, 11.4 equiv) was added at 60-70° C., and the mixture was stirred at this temperature for 2 hr. The mixture was cooled to −5-5° C. Ester 1b (20 g, 1.00 equiv) in THF (52 mL) solution was added at −5-5° C., and the mixture was stirred at this temperature for 1 hr. The reaction was deemed completed as determined by HPLC. 10% citric acid aqueous solution (160 mL) and EtOAc (400 mL) were successively added at 20-30° C. The mixture was stirred at 20-30° C. for 30 min. The separated organic portion was washed with 20% NaCl aqueous solution (13 L). The separated organic portion was concentrated at 35-45° C. under reduced pressure. EtOAc (350 mL) was added at 20-30° C. The mixture was heated to 60-65° C. for dissolution, and n-heptane (175 mL) was added at this temperature. The mixture was stirred at 60-65° C. for 3 hr before being cooled to 0-5° C. The mixture was filtered, and the filtered cake was washed with n-heptane (126 mL). After being dried at 40-50° C. under reduced pressure, 2b (12.46 g, 54% yield) was obtained as a yellow solid.

$^1$H NMR (400 MHz, CDCl$_3$) δ 7.38-7.17 (m, 10H), 5.63 (d, J=7.2 Hz, 1H), 5.10 (s, 2H), 4.59 (dd, J=13.6, 7.6 Hz, 1H), 4.07 (d, J=14.0 Hz, 1H), 3.59 (d, J=14.0 Hz, 1H), 3.20 (dd, J=14.0, 6.0 Hz, 1H), 3.01 (dd, J=14.0, 8.0 Hz, 1H), 2.68 (s, 3H)

Example 3

Preparation of (3S)-3-[di(phenylmethyl)amino]-1-(methylsulfilnyl)-4-phenylbutan-2-one 2c To a suitable reactor was added THF (94 mL) and NaH (60%, 2.76 g, 3.0 equiv) at 20-30° C. under N$_2$. The white slurry was heated to 60-70° C. DMSO (19 mL, 11.6 equiv) was added at 60-70° C., and the mixture was stirred at this temperature for 2 hr. The mixture was cooled to −5-5° C. Ester 1c (10 g, 1.00 equiv) in toluene (95 mL) solution was added at −5-5° C., and the mixture was stirred at this temperature for 1 hr. The reaction was deemed completed as determined by TLC. 10% citric acid aqueous solution (110 mL) and EtOAc (135 mL) were successively added at 20-30° C. The mixture was stirred at 20-30° C. for 30 min. The separated organic portion was washed with 20% NaCl aqueous solution (30 mL). The separated organic portion was concentrated at 35-45° C. under reduced pressure. The resulting crude products were purified by flash column chromatography (EtOAc/n-heptane=2/1) to afford a diastereomeric mixture of 2c (6.06 g, 65% yield) as a white solid.

$^1$H NMR (400 MHz, CDCl$_3$) δ 7.42-7.15 (m, 15H), [4.09 (d, J=14.4 Hz, minor isomer), 4.03 (d, J=14.4 Hz, major isomer), totaling 1H], 3.88 (d, J=13.6 Hz, 2H), 3.67-3.59 (m, 2H), 3.59 (d, J=13.6 Hz, 2H), 3.19 (dd, J=3.4, 13.2 Hz, 1H), 3.01 (dd, J=3.6, 13.6 Hz, 1H), [2.38 (s, minor isomer), 2.30 (s, major isomer), totaling 3H]

Example 4

Preparation of 1,1-dimethylethyl N-[(1S)-1-methyl-3-(methylsulfinyl)-2-oxopropyl]carbamate 2d To a suitable reactor was added THF (94 mL) and NaH (60%, 18 g, 3.0 equiv) at 20-30° C. under $N_2$. The white slurry was heated to 60-70° C. DMSO (190 mL, 17.7 equiv) in THF (250 mL) solution was added at 60-70° C., and the mixture was stirred at this temperature for 2.5 hr. The mixture was cooled to −5-5° C. Ester 1d (30.6 g, 1.00 equiv) in THF (95 mL) solution was added at −5-5° C., and the mixture was stirred at this temperature for 1 hr. The reaction was deemed completed as determined by TLC. 10% citric acid aqueous solution (720 mL) and EtOAc (1.6 L) were successively added at 20-30° C. The mixture was stirred at 20-30° C. for 30 min. The separated organic portion was washed with 20% NaCl aqueous solution (180 mL). The separated organic portion was concentrated at 35-45° C. under reduced pressure. The resulting crude products were purified by flash column chromatography (EtOAc/n-heptane=2/1) to afford a diastereomeric mixture of 2d (23.69 g, 63% yield) as a yellow oil.

$^1$H NMR (400 MHz, $CDCl_3$) δ [5.48 (m, major isomer), 5.38 (m, minor isomer), totaling 1H], 4.32-4.15 (m, 1H), 4.14-4.02 (m, 1H), [3.86 (d, J=14.0 Hz, major isomer), 3.81 (d, J=14.0 Hz, minor isomer), totaling 1H], [2.72 (s, minor isomer), 2.71 (s, major isomer), totaling 3H], 1.43 (s, 9H), 1.34 (d, J=7.2 Hz, 3H)

Example 5

Preparation of 1,1-dimethylethyl N-[(1S)-1-(1-methylethyl)-3-(methylsulfinyl)-2-oxopropyl]carbamate 2e To a suitable reactor was added THF (94 mL) and NaH (60%, 18 g, 3.0 equiv) at 20-30° C. under $N_2$. The white slurry was heated to 60-70° C. DMSO (190 mL, 17.7 equiv) in THF (250 mL) solution was added at 60-70° C., and the mixture was stirred at this temperature for 2.5 hr. The mixture was cooled to −5-5° C. Ester 1e (34.9 g, 1.00 equiv) in THF (95 mL) solution was added at −5-5° C., and the mixture was stirred at this temperature for 1 hr. The reaction was deemed completed as determined by TLC. 10% citric acid aqueous solution (720 mL) and EtOAc (1.6 L) were successively added at 20-30° C. The mixture was stirred at 20-30° C. for 30 min. The separated organic portion was washed with 20% NaCl aqueous solution (180 mL). The separated organic portion was concentrated at 35-45° C. under reduced pressure. The resulting crude products were purified by flash column chromatography (EtOAc/n-heptane=2/1) to afford a diastereomeric mixture of 2e (25.93 g, 62% yield) as a yellow oil.

$^1$H NMR (400 MHz, $CDCl_3$) δ [5.23 (m, minor isomer), 5.11 (m, major isomer), totaling 1H], 4.27-4.16 (m, 1H), [4.12 (d, J=14.4 Hz, major isomer), 3.99 (d, J=14.4 Hz, minor isomer), totaling 1H], [3.88 (d, J=14.4 Hz, major isomer), 3.78 (d, J=14.4 Hz, minor isomer), totaling 1H], [2.74 (s, major isomer), 2.73 (s, minor isomer), totaling 3H], 2.34-2.24 (m, 1H), 1.47 (s, 9H), [1.04 (d, J=6.8 Hz, major isomer), 1.03 (d, J=6.8 Hz, minor isomer), totaling 3H], [0.90 (d, J=6.8 Hz, major isomer), 0.87 (d, J=6.8 Hz, minor isomer), totaling 3H]

Example 6

Preparation of 1,1-dimethylethyl N-(1S)-3-methyl-1-[2-(methylsulfinyl)acetyl]butylcarbamate 2f To a suitable reactor was added THF (94 mL) and NaH (60%, 18 g, 3.0 equiv) at 20-30° C. under $N_2$. The white slurry was heated to 60-70° C. DMSO (190 mL, 17.7 equiv) in THF (189 mL) solution was added at 20-30° C., and the mixture was stirred at this temperature for 2.5 hr. The mixture was cooled to −5-5° C. Ester 1f (37 g, 1.00 equiv) in THF (95 mL) solution was added at −5-5° C., and the mixture was stirred at this temperature for 1 hr. The reaction was deemed completed as determined by TLC. 10% citric acid aqueous solution (720 mL) and EtOAc (1.6 L) were successively added at 20-30° C. The mixture was stirred at 20-30° C. for 30 min. The separated organic portion was washed with 20% NaCl aqueous solution (180 mL). The separated organic portion was concentrated at 35-45° C. under reduced pressure. The resulting crude products were purified by flash column chromatography (100% EtOAc) to afford a diastereomeric mixture of 2f (6.06 g, 65% yield) as a yellow oil.

$^1$H NMR (400 MHz, $CDCl_3$) δ [5.27 (m, major isomer), 5.17 (m, minor isomer), totaling 1H], 4.28-4.15 (m, 1H), 4.07 (d, J=14 Hz, 1H), 3.83 (d, J=14 Hz, 1H), [2.74 (s, minor isomer), 2.72 (s, major isomer), totaling 3H], 1.74-1.39 (m, 3H), 1.44 (s, 9H), 0.95 (d, J=6.8 Hz, 6H)

Example 7

Preparation of 1,1-dimethylethyl (2S)-2-[2-(methylsulfinyl)acetyl]tetrahydro-1H-1-pyrrolecarboxylate 2g To a suitable reactor was added THF (126 mL) and NaH (60%, 24.1 g, 3.0 equiv) at 20-30° C. under $N_2$. The white slurry was heated to 60-70° C. DMSO (253 mL, 17.7 equiv) in THF (253 mL) solution was added at 60-70° C., and the mixture was stirred at this temperature for 2.5 hr. The mixture was cooled to −5-5° C. Ester 1g (46.3 g, 1.00 equiv) in THF (126 mL) solution was added at −5-5° C., and the mixture was stirred at this temperature for 1 hr. The reaction was deemed completed as determined by TLC. 10% citric acid aqueous solution (960 mL) and EtOAc (2.2 L) were successively added at 20-30° C. The mixture was stirred at 20-30° C. for 30 min. The separated organic portion was washed with 20% NaCl aqueous solution (240 mL). The separated organic layer was concentrated at 35-45° C. under reduced pressure. The resulting crude products were purified by flash column chromatography (EtOAc/MeOH=7/1) to afford a diastereomeric mixture of 2g (30 g, 54% yield) as a yellow oil.

$^1$H NMR (400 MHz, $CDCl_3$) δ 4.38-4.26 (m, 1H), 4.04-3.68 (m, 2H), 3.63-3.39 (m, 2H), [2.76 (s, minor isomer), 2.73 (s, major isomer), totaling 3H], 2.22-1.81 (m, 4H), [1.44 (s), 1.43 (s), 1.41 (s), totaling 9H].

Examples 8-14 illustrate the conversions of compounds 2a through 2g into compounds 3a through 3g, respectively.

Example 8

Preparation of (3S)-3-([(1,1-dimethylethyl)oxy]carbonylamino)-1-(methylsulfanyl)-2-oxo-4-phenylbutyl ethanoate 3a To a suitable reactor was added DMSO (234 mL, 0.4 M) and 2a (30 g, 1 equiv) at 20-30° C. under $N_2$. 6N HCl aqueous solution (61 mL, 3.9 equiv) was added at 20-30° C., and the mixture was stirred at this temperature for 4 hr. The reaction was deemed completed as determined by HPLC. The mixture was cooled to 0-10° C., and 2% NH$_3$ aqueous solution (275 mL) was added at this temperature. The mixture was filtered, and the filtered cake was washed with water (150 mL). The wet cake was dissolved in EtOAc (315 mL) at 20-30° C. 20% NaCl aqueous solution (90 mL) was added at 20-30° C., and the mixture was stirred at this temperature for 30 min. The separated organic portion was concentrated at 40-50° C. under reduced pressure until the volume reached about 150 mL. More EtOAc (75 mL) was added at 20-30° C., and the resulting solution (about 225 mL) was used for next step.

To a suitable reactor was added the EtOAc solution (about 225 mL) reserved from previous step and pyridine (23.3 g, 3.2 equiv) at 20-30° C. under N$_2$. The mixture was cooled to 0-10° C., and acetyl chloride (17.6 g, 2.4 equiv) was added at this temperature. The mixture was warmed to 20-30° C. and stirred for 3 hr. The reaction was deemed completed as determined by HPLC. The slurry was cooled to 0-10° C., and 1N HCl aqueous solution (75 mL) was added at this temperature. The mixture was warmed to 20-30° C. and stirred for 30 min. The separated organic portion was washed with 9% NaHCO$_3$ aqueous solution (75 mL) and 5% NaCl aqueous solution (75 mL). The separated organic portion was concentrated at 40-50° C. under reduced pressure until the volume reached about 75 mL. Ethanol (78 mL) was added, and the mixture (about 153 mL) was concentrated at 40-50° C. under reduced pressure until the volume reached about 75 mL Ethanol (78 mL) was added to provide a diastereomeric mixture of crude 3a in EtOH solution (about 153 mL) which was used for next step.

$^1$H NMR (400 MHz, CDCl$_3$) δ 7.34-7.22 (m, 5H), [6.30 (s, major isomer), 6.05 (s, minor isomer), totaling 1H], 4.98 (m, 1H), 4.88 (m, 1H), 3.20 (m, 1H), 2.98 (m, 1H), 2.19 (s, 3H), 1.71 (s, 3H), 1.43 (s, 9H)

Example 9

Preparation of (3S)-1-(methylsulfanyl)-2-oxo-4-phenyl-3-([(phenylmethyl)oxy]carbonylamino)butyl ethanoate 3b To a suitable reactor was added DMSO (990 mL, 0.4 M) and 2b (42.0 g, 1 equiv) at 20-30° C. under N$_2$. 2N HCl aqueous solution (252 mL, 3.9 equiv) was added at 20-30° C., and the mixture was stirred at this temperature for 17 hr. The reaction was deemed completed as determined by HPLC. The mixture was cooled to 0-10° C., and 9% NaHCO$_3$ aqueous solution (600 mL) was added at this temperature. The resulting solid was combined with H$_2$O (840 mL) and filtered.

To a suitable reactor was added the crude solid and IPA (120 mL) at 20-30° C. under N$_2$. The mixture was heated to 40-50° C. for dissolution. H$_2$O (240 mL) was added at 40-50° C., and the homogeneous solution was cooled to 20-30° C. The mixture was further stirred at 20-30° C. for 1 hr. The mixture was filtered, and the filtered cake was washed with IPA/H$_2$O (150 mL, 1/2 (v/v)). After being dried at 40-50° C. under vacuum, the crude product was obtained as a white powder which was used for next step.

To a suitable reactor was added the reserved crude product, CH$_2$Cl$_2$ (150 mL), and pyridine (4.9 mL, 2.0 equiv) at 20-30° C. under N$_2$. The mixture was cooled to 0-10° C., and acetyl chloride (3.3 mL, 1.5 equiv) was added at this temperature. The mixture was warmed to 20-30° C. and stirred for 3 hr. The reaction was deemed completed as determined by HPLC. The mixture was cooled to 0-5° C., and 1N HCl aqueous solution (100 mL) was added at this temperature. The mixture was warmed to 20-30° C. and stirred for 3 hr. The separated organic portion was washed with 9% NaHCO$_3$ aqueous solution (100 mL) and 5% NaCl aqueous solution (25 mL). The separated organic portion was concentrated at 40-50° C. to provide the crude 3b which was used for next step.

$^1$H NMR (400 MHz, CDCl$_3$) δ 7.38-7.24 (m, 10H), 6.18 (s, 1H), 5.16-5.01 (m, 4H), 3.20 (dd, J=7.6, 13.6 Hz, 1H), 2.98 (dd, J=7.2, 13.6 Hz, 1H), 2.17 (s, 3H), 1.77 (s, 3H)

Example 10

Preparation of (3S)-3-[di(phenylmethyl)amino]-1-(methylsulfanyl)-2-oxo-4-phenylbutyl ethanoate 3c To a suitable reactor was added DMSO (32.6 mL, 0.13 M) and 2c (1.68 g, 1.0 equiv) at 20-30° C. under N$_2$. 2N HCl aqueous solution (8.14 mL, 3.9 equiv) was added at 20-30° C., and the mixture was stirred at this temperature for 18 hr. The reaction was deemed completed as determined by TLC. The mixture was cooled to 0-10° C., and 9% NaHCO$_3$ aqueous solution (30 mL) was added at this temperature. The mixture was extracted with EtOAc (60 mL×2). The two separated organic portions were combined and washed with 20% NaCl aqueous solution (30 mL). The separated organic phase was concentrated at 40-50° C. under reduced pressure to afford the crude product which was used for next step.

To a suitable reactor was added the reserved crude product, CH$_2$Cl$_2$ (45 mL), and pyridine (1.0 mL, 3.0 equiv) at 20-30° C. under N$_2$. The mixture was cooled to 0-10° C., and acetyl chloride (0.5 mL, 1.7 equiv) was added at this temperature. The mixture was warmed to 20-30° C. and stirred for 3 hr. The reaction was deemed completed as determined by TLC. H$_2$O (10 mL) was added at 20-30° C., and the mixture was stirred at this temperature for 30 min. The separated organic portion was washed with 20% NaCl aqueous solution (10 mL). The separated organic portion was concentrated at 40-50° C. to afford the crude product 3c. The resulting crude products were purified by flash column chromatography (EtOAc/n-heptane=1/10) to give 3c (1.00 g, 54% yield) as a yellow oil.

$^1$H NMR (400 MHz, CDCl$_3$) δ 7.43-7.16 (m, 15H), 6.43 (s, 1H), 4.25 (dd, J=10.4, 3.6 Hz, 1H), 3.90 (d, J=13.2 Hz, 2H), 3.57 (d, J=13.2 Hz, 2H), 3.20 (dd, J=12.8, 10.4 Hz, 1H), 3.06 (dd, J=12.8, 3.6 Hz, 1H), 2.17 (s, 3H), 1.21 (s, 3H)

Example 11

Preparation of (3S)-3-([(1,1-dimethylethyl)oxy]carbonylamino)-1-(methylsulfanyl)-2-oxobutyl ethanoate 3d To a suitable reactor was added DMSO (150 mL, 0.13 M) and 2d (5.7 g, 1.0 equiv) at 20-30° C. under N$_2$. 2N HCl aqueous solution (45 mL, 3.9 equiv) was added at 20-30° C., and the mixture was stirred at this temperature for 24 h. The reaction was deemed completed as determined by TLC. The mixture was cooled to 0-10° C., and 9% NaHCO$_3$ aqueous solution (150 mL) was added at this temperature. The mixture was extracted with EtOAc (300 mL×2). The separated organic portions were combined and washed with 20% NaCl aqueous solution (150 mL). The separated organic portion was concentrated at 40-50° C. under reduced pressure to afford the crude product which was used for next step.

To a suitable reactor was added the reserved crude product, CH$_2$Cl$_2$ (45 mL), and pyridine (3.15 mL, 1.5 equiv) at 20-30° C. under N$_2$. The mixture was cooled to 0-10° C., and acetyl chloride (2.38 mL, 1.3 equiv) was added at this temperature. The mixture was warmed to 20-30° C. and stirred for 4 hr. The reaction was deemed completed as determined by TLC. The mixture was cooled to 0-10° C., and $H_2O$ (10 mL) was added at this temperature. The separated organic portion was washed with 20% NaCl aqueous solution (10 mL). The separated organic portion was concentrated at 40-50° C. under reduced pressure to afford the crude product 3d. The resulting crude products were purified by flash column chromatography (EtOAc/n-heptane=1/1) to provide a diastereomeric mixture of 3d (2.75 g, 58% yield) as a colorless oil.

$^1$H NMR (400 MHz, $CDCl_3$) δ [6.22 (s, minor isomer), 6.12 (s, major isomer), totaling 1H], 5.50-5.15 (m, 1H), [4.85-4.75 (m, minor isomer), 4.73-4.61 (m, major isomer), totaling 1H], [2.15 (s, major isomer), 2.14 (s, minor isomer), totaling 3H], [2.05 (s, minor isomer), 2.04 (s, major isomer), totaling 3H], 1.42 (s, 9H), [1.40 (d, J=7.6 Hz, major isomer), 1.32 (d, J=6.8 Hz, minor isomer), totaling 3H]

Example 12

Preparation of (3S)-3-([(1,1-dimethylethyl)oxy]carbonylamino)-4-methyl-1-(methylsulfanyl)-2-oxopentyl ethanoate 3e To a suitable reactor was added DMSO (100 mL, 0.4 M) and 2e (11.26 g, 1.0 equiv) at 20-30° C. under $N_2$. 2N HCl aqueous solution (78 mL, 3.9 equiv) was added at 20-30° C., and the mixture was stirred at this temperature for 18 hr. The reaction was deemed completed as determined by TLC. The mixture was cooled to 0-10° C., and 9% $NaHCO_3$ aqueous solution (100 mL) was added at this temperature. The mixture was extracted with EtOAc (240 mL×2). The separated organic portions were combined and washed with 20% NaCl aqueous solution (100 mL). The separated organic phase was concentrated at 40-50° C. under reduced pressure to afford the crude product which was used for next step.

To a suitable reactor was added the reserved crude product, $CH_2Cl_2$ (45 mL), and pyridine (2.5 mL, 1.5 equiv) at 20-30° C. under $N_2$. The mixture was cooled to 0-10° C., and acetyl chloride (1.9 mL, 1.3 equiv) was added at this temperature. The mixture was warmed to 20-30° C. and stirred for 3 hr. The reaction was deemed completed as determined by TLC. $H_2O$ (10 mL) was added at 20-30° C., and the mixture was stirred at this temperature for 30 min. The separated organic portion was washed with 20% NaCl aqueous solution (10 mL). The separated organic portion was concentrated at 40-50° C. under reduced pressure to afford the crude product 3e. The resulting crude products were purified by flash column chromatography (EtOAc/n-heptane=1/10) to give a diastereomeric mixture of 3e (5.75 g, 45% yield) as a yellow oil.

$^1$H NMR (400 MHz, $CDCl_3$) δ 6.15 (s, 1H), 5.03-4.85 (m, 1H), 4.46 (dd, J=6.8, 3.2 Hz, 1H), 2.25-2.15 (m, 1H), [2.16 (s, minor isomer), 2.15 (s, major isomer), totaling 3H], [2.08 (s, major isomer), 2.05 (s, minor isomer), totaling 3H], [1.45 (s, major isomer), 1.44 (s, minor isomer), totaling 9H], [1.04 (d, J=7.2 Hz, minor isomer), 0.95 (d, J=6.8 Hz, major isomer), totaling 3H], [0.91 (d, J=6.4 Hz, major isomer), 0.81 (d, J=6.8 Hz, minor isomer), totaling 3H]

Example 13

Preparation of (3S)-3-([(1,1-dimethylethyl)oxy]carbonylamino)-5-methyl-1-(methylsulfanyl)-2-oxohexyl ethanoate 3f To a suitable reactor was added DMSO (129 mL, 0.4 M) and 2f (15.08 g, 1.0 equiv) at 20-30° C. under $N_2$. 6N HCl aqueous solution (34 mL, 3.9 equiv) was added at 20-30° C., and the mixture was stirred at this temperature for 18 hr. The reaction was deemed completed as determined by TLC. The mixture was cooled to 0-10° C., and 9% $NaHCO_3$ aqueous solution (120 mL) was added at this temperature. The mixture was extracted with EtOAc (300 mL×2). The separated organic portions were combined and washed with 20% NaCl aqueous solution (120 mL). The separated organic portion was concentrated at 40-50° C. under reduced pressure to afford the crude product which was used for next step.

To a suitable reactor was added the reserved crude product, $CH_2Cl_2$ (61 mL), and pyridine (4.5 mL, 1.5 equiv) at 20-30° C. under $N_2$. The mixture was cooled to 0-10° C., and acetyl chloride (3.4 mL, 1.3 equiv) was added at this temperature. The mixture was warmed to 20-30° C. and stirred for 3 hr. The reaction was deemed completed as determined by TLC. $H_2O$ (15 mL) was added at 20-30° C., and the mixture was stirred at this temperature for 30 min. The separated organic portion was washed with 20% NaCl aqueous solution (15 mL). The separated organic portion was concentrated at 40-50° C. under reduced pressure to afford the crude product 3f. The resulting crude products were purified by flash column chromatography (EtOAc/n-heptane=1/20) to give a diastereomeric mixture of 3f (8.59 g, 50% yield) as a yellow oil.

$^1$H NMR (400 MHz, $CDCl_3$) δ [6.22 (s, minor isomer), 6.16 (s, major isomer), totaling 1H], 4.91-4.49 (m, 2H), [2.16 (s, major isomer), 2.15 (s, minor isomer), totaling 3H], [2.064 (s, minor isomer), 2.062 (s, major isomer), totaling 3H], 1.87-1.55 (m, 2H), 1.53-1.33 (m, 1H), 1.44 (s, 9H), 0.99-0.86 (m, 6H)

Example 14

Preparation of 1,1-dimethylethyl (2S)-2-[2-(acetyloxy)-2-(methylsulfanyl)acetyl]tetrahydro-1H-1-pyrrolecarboxylate 3g To a suitable reactor was added DMSO (250 mL) and 2g (27.54 g, 1.0 equiv) at 20-30° C. under $N_2$. 6N HCl aqueous solution (65 mL, 3.9 equiv) was added at 20-30° C., and the mixture was stirred at this temperature for 18 hr. The reaction was deemed completed as determined by TLC. The mixture was cooled to 0-10° C., and 9% $NaHCO_3$ aqueous solution (200 mL) was added at this temperature. The mixture was extracted with EtOAc (600 mL×2). The separated organic portions were combined and washed with 20% NaCl aqueous solution (150 mL). The separated organic portion was concentrated at 40-50° C. under reduced pressure to afford the crude product which was used for next step.

To a suitable reactor was added the above crude product, $CH_2Cl_2$ (80 mL), and pyridine (5.8 mL, 1.5 equiv) at 20-30° C. under $N_2$. The mixture was cooled to 0-10° C., and acetyl chloride (4.4 mL, 1.3 equiv) was added at this temperature. The mixture was warmed to 20-30° C. and stirred for 3 hr. The reaction was deemed completed as determined by TLC. $H_2O$ (15 mL) was added at 20-30° C., and the mixture was stirred at this temperature for 30 min. The separated organic portion was washed with 20% NaCl aqueous solution (15 mL). The separated organic portion was concentrated at 40-50° C. under reduced pressure to afford the crude 3g. The resulting crude products were purified by flash column chromatography (EtOAc/n-heptane=1/20) to give a diastereomeric mixture of 3g (13.66 g, 43% yield) as a yellow oil.

$^1$H NMR (400 MHz, $CDCl_3$) δ [6.41 (s, minor isomer), 6.26 (s, major isomer), totaling 1H], [4.66 (m, minor isomer), 4.54 (m, major isomer), totaling 1H], 3.61-3.33 (m, 2H), 2.29-1.82 (m, 4H), [2.18 (s, major isomer), 2.17 (s, minor isomer), totaling 3H], 2.07 (s, 3H), [1.44 (s, minor isomer), 1.42 (s, major isomer), totaling 9H]

Examples 15-21 illustrate the conversions of compounds 3a through 3g into compounds 4a through 4g, respectively.

Example 15

Preparation of (3S)-3-([(1,1-dimethylethyl)oxy]carbonylamino)-2-hydroxy-4-phenylbutyl ethanoate 4a To a suitable reactor was added the crude 3a in EtOH solution (about 153 mL) reserved from the previous step at 20-30° C. under $N_2$. The mixture was cooled to −25 to −15° C., and $NaBH_4$ (2.35 g) in water (60 mL) was added at below −8° C. The reaction mixture was warmed to −5-5° C. and stirred for 1 hr. The reaction was deemed completed as determined by TLC. 1N HCl aqueous solution (60 mL) was added at below 10° C. The mixture was warmed to 20-30° C., and $H_2O$ (183 mL) was added at this temperature. After being stirred at 20-30° C. for 1 hr, the mixture was further cooled to 0-5° C. and stirred for 1 hr. The mixture was filtered, and the filtered cake was washed with cold 50% EtOH aqueous solution (30 mL). The combined filtrate and washing was concentrated at 40-50° C. under reduced pressure to afford crude 4a as a white powder (18.7 g).

To a suitable reactor was added crude 4a (18.7 g) and toluene (224 mL) at 20-30° C. under $N_2$. The mixture was heated to about 60° C. for dissolution. The homogeneous solution was cooled to 20-30° C. and stirred for 1 hr. The mixture was cooled to 0-5° C. and stirred for 1 hr. The mixture was filtered, and the filtered cake was washed with cold toluene (19 mL). The wet cake was dried at 40-50° C. under reduced pressure to afford 4a as a white powder (13.8 g, 97% purity, 46% yield, three steps from 2a).

$^1$H NMR (400 MHz, $CDCl_3$) δ7.34-7.22 (m, 5H), 4.61 (br d, J=6.4 Hz, 1H), 4.24 (dd, J=11.6, 3.2 Hz, 1H), 4.13 (dd, J=12.0, 6.8 Hz, 1H), 3.92 (br d, J=5.2 Hz, 1H), 3.89 (br s, 1H), 3.30 (br s, 1H), 2.96 (dd, J=14.0, 4.8 Hz, 1H), 2.89 (m, 1H), 2.12 (s, 3H), 1.38 (s, 9H)

Example 16

Preparation of (3S)-2-hydroxy-4-phenyl-3-([(phenylmethyl)oxy]carbonylamino)butyl ethanoate 4b To a suitable reactor was added crude 3b in EtOH (100 mL) solution at 20-30° C. under $N_2$. The mixture was cooled to −25 to −15° C., and $NaBH_4$ (0.77 g) in $H_2O$ (7.7 mL) was added at below −8° C. The reaction mixture was warmed to −10 to −5° C. and stirred for 2 hr. The reaction was deemed completed as determined by TLC. 1N HCl aqueous solution (20 mL) was added at below 10° C. The mixture was extracted with EtOAc (100 mL×2). The separated organic portions were combined and concentrated under at 40-50° C. reduced pressure to afford crude 4b. The diastereomeric ratio of crude 4b was determined to be 97/3 by HPLC analysis.

To a suitable reactor was added the reserved crude 4b and a solution of EA/n-heptane (100 mL, 1/3) at 20-30° C. under $N_2$. The mixture was heated to about 60° C. for dissolution. The homogeneous solution was cooled to 20-30° C. and stirred for 1 hr. The resulting solid was filtered and dried under at 40-50° C. under reduced pressure to give 4b as a white powder (4.62 g, 98% purity, 52% yield, three steps from 2b).

$^1$H NMR (400 MHz, $CDCl_3$) δ 7.36-7.20 (m, 10H), 5.05 (s, 2H), 4.86 (m, 1H), 4.25 (dd, J=11.6, 3.6 Hz, 1H), 4.15 (dd, J=11.6, 6.8 Hz, 1H), 4.01 (m, 1H), 3.92 (m, 1H), 3.01-2.92 (m, 2H), 2.12 (s, 3H)

Example 17

Preparation of (3S)-3-[di(phenylmethyl)amino]-2-hydroxy-4-phenylbutyl ethanoate 4c To a suitable reactor was added 3c (2.2 g, 1.0 eq) and EtOH (11 mL) at 20-30° C. under $N_2$. The mixture was cooled to −25 to −15° C., and $NaBH_4$ (304.1 mg, 0.8 equiv) in $H_2O$ (4 mL) was added at below −15° C. The reaction mixture was warmed to −5-5° C. and stirred for 1 hr. The reaction was deemed complete as determined by TLC. 1N HCl aqueous solution (32 mL) was added at below 10° C., and the mixture was warmed to 20-30° C. EtOAc (200 mL) was added at 20-30° C., and the mixture was stirred at this temperature for 30 min. The separated organic portion was concentrated at 40-50° C. under reduced pressure to afford crude 4c. The diastereomeric ratio of crude 4c was determined to be 64/36 by HPLC analysis. The residue was purified by flash column chromatography (EtOAc/n-heptane=1/2) to give a diastereomeric mixture of 4c (2.20 g, 83% yield) as a yellow solid.

$^1$H NMR (400 MHz, $CDCl_3$) δ 7.40-7.22 (m, 15H), 4.07-3.94 (m, 1H), 4.05 (dd, J=11.2, 1.6 Hz, 1H), 3.99 (d, J=13.2 Hz, 1H), 3.85-3.78 (m, 2H), 3.46-3.43 (m, 2H), 3.22-3.17 (m, 1H), 3.08-3.03 (m, 1H), 2.81-2.75 (m, 1H)

Example 18

Preparation of (3S)-3-([(1,1-dimethylethyl)oxy]carbonylamino)-2-hydroxybutyl ethanoate 4d To a suitable reactor was added 3d (2.2 g, 1.0 equiv) and EtOH (11 mL) at 20-30° C. under $N_2$. The mixture was cooled to −25 to −15° C., and $NaBH_4$ (304.1 mg, 0.8 equiv) in $H_2O$ (4 mL) was added at below −15° C. The reaction mixture was warmed to −5-5° C. and stirred for 1 hr. The reaction was deemed complete as determined by TLC. 1N HCl aqueous solution (32 mL) was added at below 10° C., and the mixture was warmed to 20-30° C. EtOAc (200 mL) was added at 20-30° C., and the mixture was stirred at this temperature for 30 min. The separated organic portion was concentrated at 40-50° C. under reduced pressure to afford crude 4d. The diastereomeric ratio of crude 4d was determined to be 72/28 by HPLC analysis. The residue was purified by flash column chromatography (EtOAc/n-heptane=1/2) to give a diastereomeric mixture of 4d (2.20 g, 83% yield) as a yellow solid.

$^1$H NMR (400 MHz, $CDCl_3$) δ 4.82-4.69 (m, 1H), [4.18 (dd, J=7.2, 4.0 Hz, major isomer), 4.11 (dd, J=7.2, 4.0 Hz, minor isomer), totaling 1H], [4.08 (dd, J=7.2, 6.8 Hz, major isomer), 4.11-4.06 (m, minor isomer), totaling 1H], 3.92-3.59 (m, 2H), [2.14 (s, minor isomer), 2.11 (s, major isomer), totaling 3H], [1.46 (s, minor isomer), 1.45 (s, major isomer), totaling 9H], [1.23 (d, J=6.8 Hz, minor isomer), 1.18 (d, J=6.8 Hz, major isomer), totaling 3H]

Example 19

Preparation of (3S)-3-([(1,1-dimethylethyl)oxy]carbonylamino)-2-hydroxy-4-methylpentyl ethanoate 4e To a suitable reactor was added 3e (1.32 g, 1.0 equiv) and EtOH (26 mL) at 20-30° C. under $N_2$. The mixture was cooled to −25 to −15° C., and $NaBH_4$ (117.4 mg, 0.8 equiv) in $H_2O$ (2.6 mL) was added at below −15° C. The reaction mixture was warmed to −5-5° C. and stirred for 1 hr. The reaction was deemed completed as determined by TLC. 1N HCl aqueous solution (13 mL) was added at below 10° C., and the mixture was warmed to 20-30° C. EtOAc (160 mL) was added at 20-30° C., and the mixture was stirred at this temperature for 30 min. The separated organic portion was concentrated at 40-50° C. under reduced pressure to afford crude 4e. The diastereomeric ratio of crude 4e was determined to be 78/22 by HPLC analysis. The residue was purified by flash column chromatography (EtOAc/n-heptane=1/2) to give a diastereomeric mixture of 4e (0.92 g, 81% yield) as a yellow oil.

$^1$H NMR (400 MHz, CDCl$_3$) δ 4.54-4.46 (m, 1H), 4.27 (dd, J=11.6, 2.8 Hz, 1H), 4.10 (dd, J=11.6, 6.8 Hz, 1H), 3.89-3.81 (m, 1H), 3.69-3.58 (m, 1H), 2.87 (m, 1H), [2.14 (s, minor isomer), 2.13 (s, major isomer), totaling 3H], [1.48 (s, minor isomer), 1.47 (s, major isomer), totaling 9H], [1.01 (d, J=6.4 Hz, minor isomer), 1.00 (d, J=6.4 Hz, major isomer), totaling 3H], [0.94 (d, J=6.8 Hz, major isomer), 0.86 (d, J=6.8 Hz, minor isomer), totaling 3H]

Example 20

Preparation of (3S)-3-([(1,1-dimethylethyl)oxy]carbonylamino)-2-hydroxy-5-methylhexyl ethanoate 4f To a suitable reactor was added 3f (1.55 g, 1.0 equiv) and EtOH (30 mL) was added at 20-30° C. under N$_2$. The mixture was cooled to −25 to −15° C., and NaBH$_4$ (132.1 mg, 0.8 equiv) in H$_2$O (3.1 mL) was added at below −15° C. The reaction mixture was warmed to −5-5° C. and stirred for 1 hr. The reaction was deemed completed as determined by TLC. 1N HCl aqueous solution (13 mL) was added at below 10° C., and the mixture was warmed to 20-30° C. EtOAc (160 mL) was added at 20-30° C., and the mixture was stirred at this temperature for 30 min. The separated organic portion was concentrated at 40-50° C. under reduced pressure to afford crude 4f. The diastereomeric ratio of crude 4f was determined to be 58/42 by HPLC analysis. The residue was purified by flash column chromatography (EtOAc/n-heptane=1/2) to give a diastereomeric mixture of 4f (1.04 g, 78% yield) as a yellow solid.

$^1$H NMR (400 MHz, CDCl$_3$) δ 4.75-4.53 (m, 1H), 4.19-4.05 (m, 2H), 3.85-3.55 (m, 2H), [2.12 (s, minor isomer), 2.10 (s, major isomer), totaling 3H], 1.75-1.62 (m, 1H), 1.55-1.31 (m, 2H), 1.48 (s, minor isomer), 1.47 (s, major isomer), totaling 9H], 0.95-0.87 (m, 6H)

Example 21

Preparation of 1,1-dimethylethyl (2S)-2-[2-(acetyloxy)-1-hydroxyethyl]tetrahydro-1H-1-pyrrolecarboxylate 4g To a suitable reactor was added 3g (1.19 g, 1.0 equiv) and EtOH (6 mL) was added at 20-30° C. under N$_2$. The mixture was cooled to −25 to −15° C., and NaBH$_4$ (107.1 mg, 0.8 equiv) in H$_2$O (2.4 mL) was added at below −15° C. The reaction mixture was warmed to −5-5° C. and stirred for 1 hr. The reaction was deemed completed as determined by TLC. 1N HCl aqueous solution (11 mL) was added at below 10° C., and the mixture was warmed to 20-30° C. EtOAc (100 mL) was added at 20-30° C., and the mixture was stirred at this temperature for 30 min. The separated organic portion was concentrated under reduced pressure to afford crude 4g. The diastereomeric ratio of crude 4g was determined to be 95/5 by HPLC analysis. The residue was purified by flash column chromatography (EtOAc/n-heptane=1/1) to give a diastereomeric mixture of 4g (0.84 g, 82% yield) as a yellow oil.

$^1$H NMR (400 MHz, CDCl$_3$) δ 4.20 (dd, J=11.6, 2.4 Hz, 1H), 4.19-4.12 (m, 1H), 4.03 (dd, J=11.6, 5.6 Hz, 1H), 3.82-3.61 (m, 1H), 3.61-3.40 (m, 1H), 3.37-3.21 (m, 1H), [2.10 (s, major isomer), 2.09 (s, minor isomer), totaling 3H], 1.98-1.71 (m, 4H), [1.48 (s, major isomer), 1.47 (s, minor isomer), totaling 9H]

Examples 22-25 illustrate the synthesis of chiral aminoepoxides 6 and 8 from common precursor 4a, as shown in FIGS. 2 and 3.

Example 22

Preparation of (2S,3S)-3-[(tert-butoxycarbonyl)amino]-2-[(methylsulfonyl)oxy]-4-phenylbutyl acetate 5

To a suitable reactor was added 4a (2 g, 6.18 mmol), CH$_2$Cl$_2$ (20 mL), DMAP (0.15 g, 1.24 mmol), and Et$_3$N (1.37 g, 13.61 mmol) at 20-30° C. under N$_2$. The mixture was cooled to 0-5° C., and MsCl (1.4 g, 12.36 mmol) in CH$_2$Cl$_2$ (3 mL) solution was added at this temperature. The mixture was warmed to 20-30° C. and stirred for 1 hr. H$_2$O (10 mL) was added at 20-30° C., and the mixture was stirred at this temperature for 30 min. The separated organic portion was washed with 20% NaCl aqueous solution (10 mL). The separated organic portion was concentrated at 40-50° C. under reduced pressure to afford 5 (2.8 g) as a yellow solid in quantitative yield.

$^1$H NMR (400 MHz, CDCl$_3$) δ 7.35-7.22 (m, 5H), 5.03 (br s, 1H), 4.66 (br d, J=7.6 Hz, 1H), 4.39 (d, J=12.4 Hz, 1H), 4.23 (dd, J=12.4, 7.2 Hz, 1H), 4.16 (br s, 1H), 3.12 (s, 3H), 3.03 (dd, J=14.4, 4.8 Hz, 1H), 2.76 (t, J=10.8 Hz, 1H), 2.12 (s, 3H), 1.36 (s, 9H)

Example 23

Preparation of tert-butyl N-{(1S)-1-[(2R)oxiran-2-yl]-2-phenylethyl}carbamate 6

To a suitable reactor was added 5 (2 g, 4.98 mmol), THF (20 mL), MeOH (20 mL), and K$_2$CO$_3$ (1.5 g, 10.96 mmol) at 20-30° C. under N$_2$. The mixture was stirred at 20-30° C. for 15 hr. The mixture was filtered, and the filtrate was concentrated at 40-50° C. under reduced pressure to yield a pale yellow oil. After being purified by flash column chromatography, 6 was obtained as a white solid in 90% yield.

$^1$H NMR (400 MHz, CDCl$_3$) δ 7.35-7.23 (m, 5H), 4.51 (br s, 1H), 4.14 (br d, J=6.8 Hz, 1H), 3.04-2.96 (m, 2H), 2.90 (dd, J=13.2, 7.6 Hz, 1H), 2.71 (t, J=4.4 Hz, 1H), 2.60 (br s, 1H), 1.41 (s, 9H)

Example 24

Preparation of (2S,3S)-3-(tert-Butoxycarbonyl)amino-4-phenyl-1,2-butane-diol 7

To a suitable reactor was added 4a (52.3 g, 162 mmol), MeOH (810 mL), and 25% NaOMe/MeOH (8.1 mmol) at 20-30° C. under N$_2$. The mixture was stirred at 20-30° C. for 2 hr, and 1 N HCl aqueous solution (16.2 mmol) was added at this temperature. The separated organic portion was concentrated at 40-50° C. under reduced pressure. Toluene (1100 mL) was added and the mixture was heated to 108-110° C. for dissolution. The mixture was cooled to 45-50° C. and stirred for 30 min. The mixture was further cooled to 20-30° C. and stirred for 1 hr. The mixture was filtered, and the filtered cake was washed with toluene (220 mL). The wet cake was dried at 40-50° C. under reduced pressure to give diol 7 as an off-white to white powder (39.5 g, 87% yield).

$^1$H NMR (400 MHz, CDCl$_3$) δ 7.37-7.25 (m, 5H), 4.58 (d, J=8.4 Hz, 1H), 3.90-3.83 (m, 1H), 3.72-3.62 (m, 2H), 3.38 (br, 2H), 3.12 (dd, J=14.0, 3.6 Hz, 1H), 2.93 (dd, J=14.2, 7.8 Hz, 1H), 2.83 (d, J=8.8 Hz, 1H), 1.41 (s, 9H)

Example 25

Preparation of (2S,3S)-3-(tert-Butoxycarbonyl) amino-1,2-epoxy-4-phenylbutane 8

To a suitable reactor was added diol 7 (10.2 g, 36.4 mmol), dibutyltin oxide (181 mg, 0.73 mmol), tosyl chloride (8.30 g, 43.5 mmol), and NMP (50 mL) at 20-30° C. under N$_2$. NEt$_3$ (6.1 mL, 43.9 mmol) was added at 20-30° C., and the mixture was stirred at this temperature for 1 hr. H$_2$O (100 mL) was added at 20-30° C., and the mixture was stirred at this temperature for 1 hr. The mixture was filtered, and the filtered cake was washed with and aqueous 25% MeOH solution (60 mL). The wet cake was dried at 40-50° C. under reduced pressure to give the tosyl compound as an off-white solid.

To a suitable reactor was added the tosylate reserved from the previous step, MeOH (120 mL), and 25% NaOMe/MeOH solution (44 mmol) at 20-30° C. under N$_2$. After being stirred at 20-30° C. for 1 hr, the mixture was cooled to 0-10° C. H$_2$O (240 mL) was added at 0-10° C., and the mixture was stirred at this temperature for 10 min. The mixture was filtered, and the filtered cake was washed with aqueous 25% MeOH (180 mL). The wet cake was dried at 40-50° C. under reduced pressure to give epoxide 8 as a white powder (8.32 g, 87% yield, two steps from 7).

$^1$H NMR (400 MHz, CDCl$_3$) δ 7.36-7.24 (m, 5H), 4.46 (br, 1H), 3.72 (br, 1H), 2.99 (dd, 14.0, 5.2 Hz, 1H), 2.95-2.86 (m, 2H), 2.82 (dd, J=4.4, 4.4 Hz, 1H), 2.78 (br, 1H), 1.41 (s, 9H)

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A process for preparing a compound of formula 4:

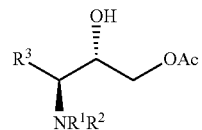

said process comprising contacting a compound of formula 3:

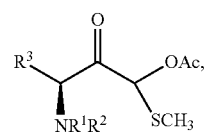

with a reducing agent to produce said compound of formula 4, in a diastereomeric ratio of at least 58/42, wherein
$R^1$ is selected from the group consisting of hydrogen, branched or unbranched C$_1$-C$_6$ alkyl and C$_7$-C$_{18}$ aralkyl;
$R^2$ is an amine protecting group; and
$R^3$ is selected from the group consisting of branched or unbranched C$_1$-C$_6$ alkyl and C$_7$-C$_{18}$ aralkyl, or
$R^3$ and $R^1$ together form a 4- to 7-membered cyclic group having from 3 to 6 carbon atoms.

2. The process according to claim 1, wherein said reducing agent is lithium aluminum hydride or sodium borohydride.

3. The process according to claim 1, wherein said process is carried out in the presence of a protic solvent.

4. The process according to claim 3, wherein said protic solvent is selected from the group consisting of methanol, ethanol, 1-propanol and 2-propanol.

5. The process according to claim 1, wherein said process is carried out in the presence of a mixture of ethanol and water.

6. The process according to claim 1, wherein $R^2$ is selected from the group consisting of t-butoxycarbonyl, benzyloxycarbonyl, methoxycarbonyl, or benzyl.

7. The process according to claim 1, wherein said process is carried out at about −40° C. to room temperature.

8. A process in accordance with claim 1, wherein $R^1$ is H, $R^2$ is t-butoxycarbonyl or benzyloxycarbonyl, and $R^3$ is isopropyl, methyl or benzyl; and the compound of formula 4 is produced in a diastereomeric ratio of at least 72/28.

9. A process in accordance with claim 1, wherein $R^1$ and $R^3$ together form a 5-membered cyclic group; and the compound of formula 4 is produced in a diastereomeric ratio of about 95/5.

* * * * *